US010247606B2

(12) United States Patent
Malcolm et al.

(10) Patent No.: US 10,247,606 B2
(45) Date of Patent: Apr. 2, 2019

(54) LONG WAVELENGTH INFRARED DETECTION AND IMAGING WITH LONG WAVELENGTH INFRARED SOURCE

(71) Applicant: ITI Scotland—Scottish Enterprise, Glasgow (GB)

(72) Inventors: Graeme Malcolm, Scotland (GB); Gordon Robertson, Scotland (GB)

(73) Assignee: ITI SCOTLAND—SCOTTISH ENTERPRISE, Glasgow (GB)

( * ) Notice: Subject to any disclaimer, the term of this patent is extended or adjusted under 35 U.S.C. 154(b) by 18 days.

(21) Appl. No.: 14/424,933

(22) PCT Filed: Aug. 30, 2013

(86) PCT No.: PCT/GB2013/052279
§ 371 (c)(1),
(2) Date: Feb. 27, 2015

(87) PCT Pub. No.: WO2014/033465
PCT Pub. Date: Mar. 6, 2014

(65) Prior Publication Data
US 2015/0260572 A1    Sep. 17, 2015

(30) Foreign Application Priority Data

Aug. 30, 2012 (GB) .................................. 1215423.3
Feb. 5, 2013 (GB) .................................. 1302026.8

(51) Int. Cl.
*G01J 3/10* (2006.01)
*G01N 21/3504* (2014.01)
(Continued)

(52) U.S. Cl.
CPC ................ *G01J 3/108* (2013.01); *G01J 3/42* (2013.01); *G01N 21/3504* (2013.01);
(Continued)

(58) Field of Classification Search
CPC ..... G02F 1/39; G01N 21/3581; H01S 3/1083; H01S 3/00; G01J 2003/2826; G01J 3/2823

See application file for complete search history.

(56) References Cited

U.S. PATENT DOCUMENTS 5,325,229 A * 6/1994 Millard ..................... G02F 1/39
219/389
2004/0252300 A1* 12/2004 Slater ........................ G01J 3/42
356/318

(Continued)

FOREIGN PATENT DOCUMENTS

EP           1503204 A1    2/2005
JP        2005077606 A    3/2005
(Continued)

OTHER PUBLICATIONS

Japanese Examination Report dated Aug. 17, 2017 for Japan Application No. 2015-529125 of Graeme, M. et al.

*Primary Examiner* — Kenneth J Malkowski
(74) *Attorney, Agent, or Firm* — Perkins Coie LLP (57) ABSTRACT

An infrared detection system comprises the following elements. A laser source provides radiation for illuminating a target (5). This radiation is tuned to at least one wavelength in the fingerprint region of the infrared spectrum. A detector (32) detects radiation backscattered from the target (5). An analyzer determines from at least the presence or absence of detected signal in said at least one wavelength whether a predetermined volatile compound is present. An associated detection method is also provided. In embodiments, the laser source is tunable over a plurality of wavelengths, and the detector comprises a hyperspectral imaging system. The laser source may be an optical parametric device has a laser gain medium for generating a pump beam in a pump laser cavity, a pump laser source and a nonlinear medium com- (Continued)

prising a ZnGeP2 (ZGP) crystal. On stimulation by the pump beam, the ZnGeP2 (ZGP) crystal is adapted to generate a signal beam having a wavelength in a fingerprint region of the spectrum and an idler beam having a wavelength in the mid-infrared region of the spectrum. The laser gain medium and the ZnGeP2 (ZGP) crystal are located in the pump wave cavity.

12 Claims, 5 Drawing Sheets

(51) Int. Cl.
    *H01S 3/108*     (2006.01)
    *G01N 21/359*     (2014.01)
    *G01J 3/42*     (2006.01)
    *G01N 21/47*     (2006.01)
    *G01N 21/49*     (2006.01)
    *H01S 3/081*     (2006.01)
    *H01S 3/094*     (2006.01)
    *H01S 3/117*     (2006.01)
    *H01S 3/16*     (2006.01)
    *H01S 3/082*     (2006.01)
    *H01S 3/11*     (2006.01)
    *G01V 8/00*     (2006.01)
(52) U.S. Cl.
    CPC ....... *G01N 21/359* (2013.01); *G01N 21/4738* (2013.01); *G01N 21/49* (2013.01); *H01S 3/081* (2013.01); *H01S 3/094* (2013.01); *H01S 3/1083* (2013.01); *H01S 3/117* (2013.01); *H01S 3/163* (2013.01); *G01N 2021/4769* (2013.01); *G01N 2201/06113* (2013.01); *G01V 8/005* (2013.01); *H01S 3/082* (2013.01); *H01S 3/11* (2013.01); *H01S 3/161* (2013.01); *H01S 3/1643* (2013.01)

(56) References Cited

U.S. PATENT DOCUMENTS

| | | | | |
|---|---|---|---|---|
| 2006/0050749 | A1* | 3/2006 | Setzler | G02F 1/39 372/22 |
| 2008/0198365 | A1* | 8/2008 | Treado | G01J 3/02 356/73 |
| 2009/0066947 | A1* | 3/2009 | Bangalore | G01N 21/31 356/317 |
| 2009/0122816 | A1* | 5/2009 | Wagner | H01S 3/1068 372/20 |
| 2009/0141281 | A1* | 6/2009 | Stothard | G01N 21/35 356/437 |
| 2011/0116158 | A1* | 5/2011 | Dunn | H01S 3/136 359/330 |
| 2013/0044769 | A1* | 2/2013 | Nettleton | H01S 3/025 372/10 |

FOREIGN PATENT DOCUMENTS

| | | | |
|---|---|---|---|
| JP | 2008026190 A | 2/2008 | |
| JP | 2008542716 A | 11/2008 | |
| JP | 2009527775 A | 7/2009 | |
| WO | 2006061567 A1 | 6/2006 | |
| WO | WO 2006061567 A1 * | 6/2006 | ............ G01N 21/35 |
| WO | 2006127722 A2 | 11/2006 | |
| WO | 2007098034 A2 | 8/2007 | |

* cited by examiner

LONG WAVELENGTH INFRARED DETECTION AND IMAGING WITH LONG WAVELENGTH INFRARED SOURCE

CROSS-REFERENCE TO RELATED APPLICATIONS

This application is a 35 USC § 371 application of International Application No. PCT/GB2013/052279 filed Aug. 30, 2013, which claims priority to Great Britain Patent Application Nos. GB 1215423.3 filed Aug. 30, 2012, and GB 1302026.8, filed Feb. 5, 2013. The contents of the above-identified applications are incorporated herein by reference in their entireties.

FIELD OF INVENTION

The present invention relates to a method and apparatus for long wavelength infrared detection and, in preferred embodiments, hyperspectral detection and hyperspectral imaging. It also relates to an optical parametric device useful in this context. The present invention is particularly relevant to real time standoff detection, and in particular detection of volatile substances in real world environments.

BACKGROUND OF INVENTION

There are a number of practical applications for remote detection and, if possible, imaging of gaseous species present in a low concentration. These include remote detection of leaks of inflammable or poisonous materials and remote detection of explosives. At present, it is difficult to detect and particularly to image materials remotely in sufficiently low concentrations, because the available techniques are not sufficiently powerful to detect materials in low concentrations reliably or sufficiently able to discriminate relevant species.

One particularly promising technique is back-scatter absorption gas imaging (BAGI). This technique involves providing a source of light tuned to a wavelength where the target species has an absorption band, and a detector for detecting light scattered from a target area. The presence of gas will occlude an image of a scene from the target area captured where there is no gas absorption (for example, at another wavelength where there is no absorption from the target species).

It is desirable for the linewidth of the light source to be equal to or less than the width of the absorption band. For short chain hydrocarbon molecules, absorption bands of interest lie in the 2-4 micron range. For these parameter constraints, a particularly suitable light source is an optical parametric oscillator (OPO) using a nonlinear crystal such as periodically poled lithium niobate (PPLN). An OPO is a complex optical source which comprises a pump laser and a nonlinear crystal. The nonlinear crystal converts the pump light into two lower frequency (and hence longer wavelength) waves by virtue of a second order nonlinear optical interaction. The sum of the frequency of these two output waves is equal to the frequency of the pump input. The lower frequency (and longer wavelength) output is termed the idler, and the higher frequency (and shorter wavelength) output is termed the signal.

The use of BAGI techniques using OPO light sources has been extensively studied at Sandia National Laboratories (SNL). Representative papers from this research group include "Backscatter Absorption Gas Imaging—a New Technique for Gas Visualization" by T. G. McRae and T. J. Kulp, Applied Optics, 1993, 32(21) pp. 4037-4050; "Active infrared imagers visualize gas leaks" by T. J. Kulp and T. McRae, Laser Focus World, 1996, 32(6) p. 211; and "Demonstration of differential backscatter absorption gas imaging" by P. E. Powers et al, Applied Optics, 200, 39(9), pp. 1440-48. Systems using both continuous wave and pulsed OPOs are described, and imaging systems are described including focal-plane array cameras and rastering scanners. However, these systems are generally expensive and immobile, and not well adapted to real world applications outside a laboratory environment.

A development on this approach is described in WO 2006/061567 A1. This discloses a BAGI system using an OPO in which the pump wave laser source and the nonlinear medium are provided in the same optical cavity. This approach allows for more efficient use of pump laser power, and in combination with use of Q-switching, allows for use in a rapidly pulsed mode which can be used effectively with raster scanning to construct an image of a scene. This makes it possible to produce a less expensive and more mobile device capable of IR imaging using BAGI techniques.

While these techniques are effective to image the presence or absence of classes of material, such as short chain hydrocarbons, they lack the resolution to allow specific materials of interest to be distinguished from a more general class. This is because use of OPOs of this type only allows access to the medium wavelength infrared (MWIR) region, typically defined as extending from 3-8 μm and shorter wavelengths—for example, the working range of a PPLN OPO is typically from 2-4 μm. This MWIR region contains absorption bands which are effective to allow a specific class of material (such a ketone, an unsaturated hydrocarbon or a saturated hydrocarbon) to be recognised, but not to allow one material within that class to be distinguished from another. Recognition of individual molecular species typically requires a spectrum over a broader spectral region. Multiple spectral bands, including bands in the long wavelength infrared (LWIR), typically defined as extending from 8-15 μm, can then be used and matched with known or calculated spectra to determine the presence or absence of a particular species. The "fingerprint region" for infrared spectroscopy lies largely in the LWIR—the fingerprint region is normally taken as extending between 500 and 1500 $cm^{-1}$, or 6.67-20 μm. Spectral lines in the fingerprint region generally include relatively sharp lines which result from bending vibrations specific to the geometry of an individual molecule—these spectral lines distinguish different members of a class from each other and can thus be used to identify individual molecular species. Existing BAGI techniques cannot however work effectively in most of the signature region, as known technologies do not function effectively beyond the MWIR region.

SUMMARY OF INVENTION

Accordingly, in a first aspect the invention provides an infrared detection system, comprising: a laser source providing radiation for illuminating a target, wherein the radiation is tuned to at least one wavelength in the fingerprint region of the infrared spectrum; a detector configured to detect radiation backscattered from the target; and an analyser adapted to match detected radiation signals against predetermined spectra to determine from at least the presence or absence of detected signal in said at least one wavelength whether a predetermined volatile compound is present.

This arrangement allows for effective identification of the presence or absence of specific volatile compounds in remote detection.

Advantageously, the laser source comprises an optical parametric oscillator having a pump laser and a nonlinear medium. Preferably, the nonlinear medium comprises a $ZnGeP_2$ (ZGP) crystal. This laser source provides good access to the fingerprint region. In one preferred arrangement, the nonlinear crystal is disposed inside a cavity of the pump laser.

In a preferred arrangement, both an idler beam and a signal beam of the optical parametric laser are provided as output radiation. Preferably, the idler beam provides output radiation at least partly within the fingerprint region and the signal beam provides output radiation at least partly at shorter wavelengths than in the fingerprint region. This is achievable using a ZGP crystal as nonlinear medium.

Preferably the system further comprises tuning means to tune the laser source between a plurality of wavelengths, wherein the infrared detection system is a hyperspectral detection system. The analyser may then be adapted to determine from the presence or absence of detected signal in more than one wavelength of the plurality of wavelengths whether a predetermined volatile compound is present.

Moreover, the analyser may be adapted to determine from the presence or absence of detected signal in wavelengths of the plurality of wavelengths whether one or more of a plurality of predetermined volatile compounds are present.

In some embodiments a plurality of laser sources are provided, comprising at two optical parametric oscillators with different nonlinear crystals.

Preferably, the one or more laser sources provide pulsed output radiation.

In a preferred arrangement, the detector comprises an imaging system and the infrared detection system comprises an imager, preferably one that provides an image in real time.

An imaging system is particularly effective in combination with pulsed output radiation from the laser sources. The infrared detection system may then comprise a scanning system for scanning a target region wherein the scanning system is synchronised with the pulsed output radiation. A pulse of radiation output by the one or more laser sources at a wavelength may then determine an image pixel value at that wavelength. This enables effective hyperspectral imaging.

Preferably, the analyser matches detected radiation signals against predetermined spectra to determine the presence or absence of the predetermined material. Where the detection system is hyperspectral, the analyser may match detected radiation signals against predetermined spectra at a plurality of wavelengths determined for that predetermined material. At least some of the plurality of wavelengths may lie in the fingerprint region. Where the detection system is an imaging system, the analyser may determine a portion of an image where a predetermined material is present or absent. The presence or absence of a predetermined material could then be represented in a false colour image.

In a second aspect, the invention provides a method of determining the presence or absence of a predetermined volatile compound comprising: illuminating a target with radiation from a laser source tuned to at least one wavelength in the fingerprint region of the infrared spectrum; detecting radiation backscattered from the target; and determining by matching detected radiation signals against predetermined spectra from at least the presence or absence of detected signal in said at least one wavelength whether a predetermined volatile compound is present.

According to a third aspect of the present invention there is provided an optical parametric device having a laser gain medium for generating a pump beam in a pump laser cavity, a pump laser source and a nonlinear medium comprising a ZnGeP2 (ZGP) crystal, wherein on stimulation by the pump beam, the ZnGeP2 (ZGP) crystal is adapted to generate a signal beam having a wavelength in a fingerprint region of the spectrum and an idler beam having a wavelength in the mid-infrared region of the spectrum, and wherein the laser gain medium and the ZnGeP2 (ZGP) crystal are located in the pump laser cavity.

Preferably, the pump laser source comprises a Ho:YAG laser.

Using this approach, an intra-cavity optical parametric oscillator may be formed using two beam splitter mirrors to separate the signal and idler beams from the pump beam. The beam splitter mirrors may comprise ZnSe mirrors.

Preferably, the pump beam is pulsed. In particular, the pump laser may be Q-switched, for example comprising an acousto-optic Q-switch.

In preferred embodiments, the optical parametric device is adapted for tuning the signal beam and the idler beam over a range of wavelengths. In one arrangement to achieve this, it may further comprise a rotatable motion stage, wherein the ZnGeP2 (ZGP) crystal is mounted on the rotatable motion stage and the signal and idler beams are tuned by rotation of the rotatable motion stage.

Features described above in respect of the first and second aspects of the invention may also apply to this third aspect.

BRIEF DESCRIPTION OF DRAWINGS

Specific embodiments of the invention will be described below, by way of example, with reference to the accompanying drawings, of which.

Figure 1:
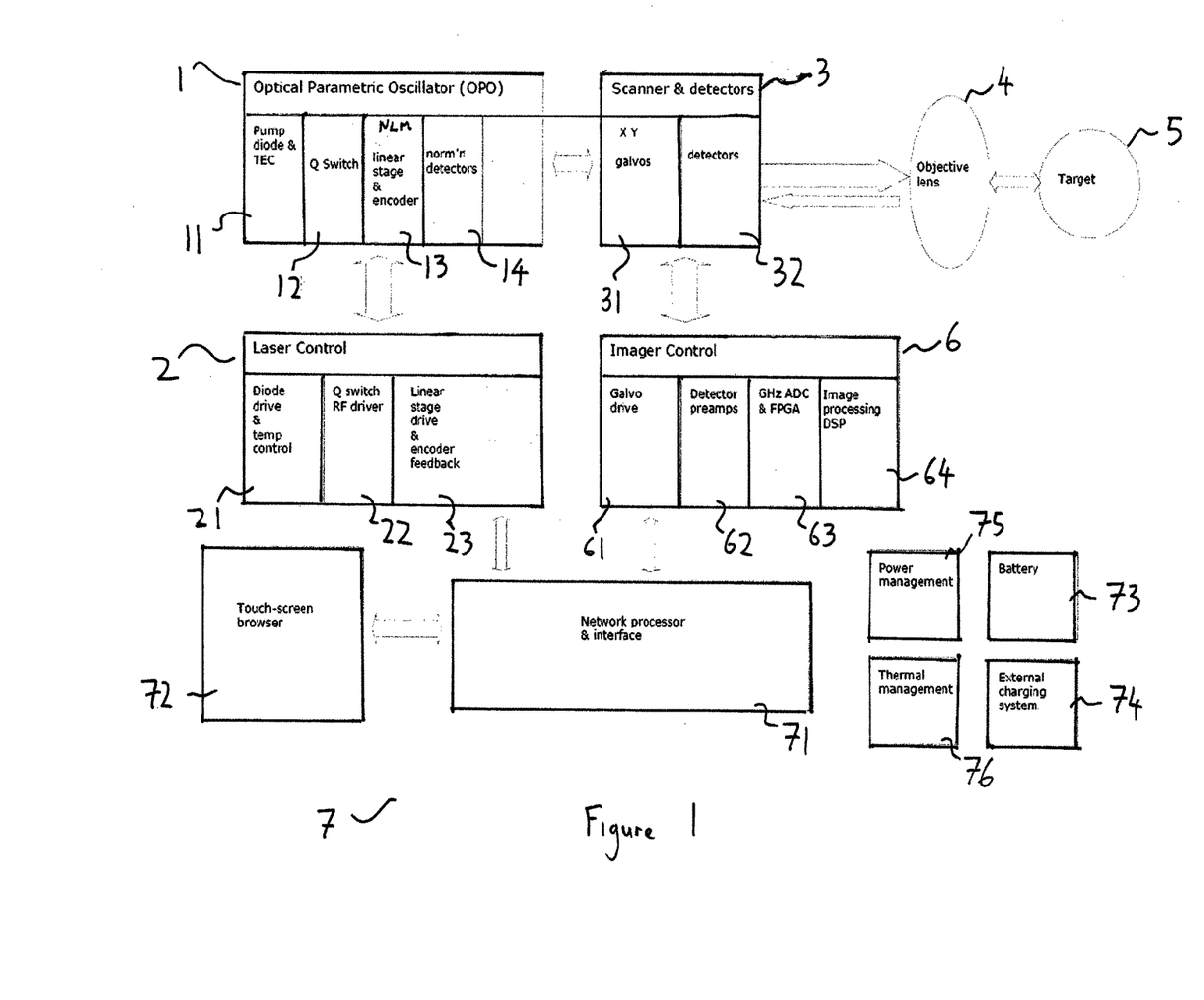
FIG. 1 shows the elements of a hyperspectral imaging system in accordance with an embodiment of the invention.

The main elements of a hyperspectral detection system—in this case, a hyperspectral imaging system, but the imaging aspect can be removed to leave a detection system—are set out in FIG. 1.

A laser source section 1 comprises one or more laser sources for providing radiation tunable between at least a plurality of wavelengths for illuminating a target. As will be discussed below, the laser source or sources extend into the LWIR region to allow for use of the fingerprint region of the infrared section. The laser source section 1 comprises in this embodiment one or more optical parametric oscillators (OPOs), though embodiments may employ other types of optical source tunable in relevant spectral regions. In a preferred arrangement there is a single OPO used for both LWIR and MWIR operation—in alternative arrangements there may be one OPO for MWIR operation and another OPO for LWIR operation. Each OPO in this embodiment requires a pump laser 11, a Q switch 12 (to enable high speed pulsed operation), a non-linear assembly 13 (as described in more detail below, but comprising a non-linear crystal and a means for moving it with respect to the pump beam to achieve tuning) and detectors 14 to measure outputs for use in calibration and control. A laser source control section 2 comprises a drive and temperature control circuit 21 for the pump laser 11, an RF driver 22 for the Q switch 12, and a stage drive and feedback system 23 for the non-linear assembly 13.

The light output by the laser source section 1 reaches the scanning part 31 of the scanning and detection assembly 3. The scanning part 31 comprises in this embodiment X and Y galvos to produce a raster scan of a target region. The rasterised output light passes through an objective lens 4 to reach the target region 5. Unabsorbed light is backscattered from the target region 5 and received through the objective lens 4 at detectors 32.

The scanning and detection assembly 3 is controlled by an imager controlling system 6. This comprises the following: a galvo drive system 61 to drive the scanning part 31; detector preamplifiers 62 to preamplify the signals received at the detectors 32 for subsequent signal processing; a signal conversion system 63 comprising an analogue to digital converter (ADC) operating at suitable speeds (GHz speeds for real time hyperspectral imaging) and a field programmable gate array (FPGA) to prepare signals for analysis, including providing appropriate gating so that detected signals are associated correctly with a particular position in a raster scan; and a digital signal processor (DSP) 64 programmed to produce hyperspectral images from the converted and gated signals. The image processing system as a whole may provide further analysis of the hyperspectral images produced by the DSP 64, the image processing system as a whole providing analysis to determine from at least the presence or absence of detected signal in one or more wavelengths within the fingerprint region whether a predetermined volatile compound is present.

The system as a whole contains further interface and control elements 7. The laser source control section 2 and the imager controlling system 6 are connected to a network processor and interface 71—this allows for user interaction with the system through a user interface 72. The system as a whole has additional systems allowing it to operate effectively as a standalone instrument—battery 73, external charging system 74, power management system 75 and thermal management system 76.

Individual sections and subsystems of this embodiment will now be described in more detail. Some features of this embodiment are described in greater detail in WO 2006/061567 A1, to which the reader is directed. Some features of this embodiment are also found in the Firefly-IR-SC device provided commercially by M Squared Lasers Limited—this device, embodying aspects of the technology described in WO 2006/061567 A1, comprises a pulsed MWIR laser system with a scanning accessory for imaging.

Figure 2:
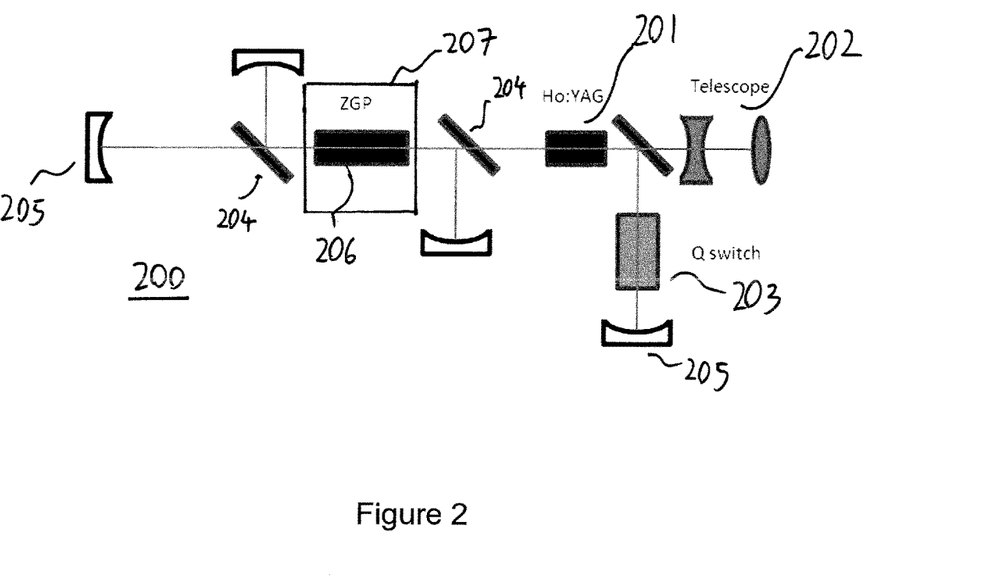
FIG. 2 shows a LWIR laser source section for use in embodiments of the invention.

FIG. 2 shows a LWIR laser source section 200 for use in embodiments of the invention. This comprises an intra-cavity OPO with Q-switching, as used in the Firefly-IR-SC device. There are however several differences in the arrangement provided here, most particularly the use of a different non-linear medium, ZGP ($ZnGeP_2$).

The non-linear material ZGP is useful for generating tunable light in the fingerprint region of the optical spectrum (6 to 10 microns). This region contains strong absorption features for many chemical groups. As is described below, by using ZGP it is also possible, from the same device, to generate light in the important 2.5 to 3.5 micron mid-infrared region which contains key absorption in hydrocarbons. Prior art approaches to use of ZGP in an optical parametric oscillator involved pumping at 2 microns using pump lasers such as Ho:YAG. The oscillation threshold of the resulting OPO is high and large pump lasers are required to make the OPO work.

In embodiments described below, reduction of the pump power required for an OPO is achieved by placing the OPO inside the pump laser cavity. This is found to increase dramatically the intra-cavity optical field, making it possible for the OPO to operate at lower pump powers.

An effective approach to achieving high intra-cavity optical fields is to keep optical losses on mirrors and in transmission of optical components within the cavity very low. ZGP has a large absorption loss at 2 microns where the Ho:YAG laser operates. This appears to suggest that placing the ZGP OPO intra-cavity within the Ho:YAG laser will not be advantageous.

In reality the Ho:YAG has a large gain and, so the system is able to support large intra-cavity losses. Even field enhancements of a factor of 2 or 3 make a significant difference in the size and practicality of the pump laser required—this can lead to reduction of pump laser power from 20 W to 8 W, makes the choice of components very much easier and reducing the overall cost of the device while increasing flexibility of design.

A further benefit of intra-cavity location is that the pump beam passes through the OPO in both directions without the need for optical isolation between the pump laser and OPO. This makes the devices more compact, cheaper and lowers the threshold further.

The individual elements of the system shown in FIG. 2 are discussed below.

The pump laser in this embodiment is a Ho:YAG laser 201, lasing at 2090 nm—this laser type is extensively used for MWIR OPOs. In this case, to provide enough power to reach the oscillation threshold for long wavelength operation, an intracavity design is used with the nonlinear crystal located within the laser cavity of the holmium-doped yttrium aluminium garnet (Ho:YAG) laser 201. The Ho:YAG laser 201 is pumped with a commercially available (for example from IPG Photonics Limited) thulium fiber laser operating at 1908 nm—in the arrangement shown, the 1908 nm fiber output is first reduced by a 3:1 telescope 202. Alternative diode lasers could be used to reduce the overall size of the system. The Ho:YAG laser 201 is Q-switched using an acousto-optic Q-switch 203 (for example, Gooch and Housego QS041-10M-H17). Both the Ho:YAG crystal and the Q-switch are water cooled. A switching rate of 20 kHz is used in this exemplary embodiment.

The intra-cavity OPO is formed using two ZnSe beam splitter mirrors 204 to separate the OPO beam from the 2090 nm pump beam and two curved end mirrors 205, with a radius of curvature 150 mm each. The spot diameter in the ZGP crystal 206 was optimized by moving the cavity mirrors to achieve a match to the pump spot size. Dielectric filters were used to ensure that no residual pump light at 2090 nm was detected. The beam splitters 204 are coated for high reflectivity at 2.8-3.3 µm and high transmission at 5-9 µm. The end mirror 205 at the output is highly reflecting at 2090 nm and highly transmitting 5-9 µm.

While an intra-cavity approach is shown here, an external cavity can also be used in embodiments of the invention. In the external cavity case, larger pump powers are required to reach threshold for the OPO, but once achieved, large output powers can be expected. In the internal cavity case, as indicated above, the threshold for OPO operation is much lower and can be achieved with more modest pumps. A low output power will often be sufficient for spectroscopic applications. As stated above, a further advantage to the intra-cavity scheme is that the pump beam is double passed through the ZGP crystal. The double pass of the pump ensures that there is signal gain in both directions. The combination of the pump enhancement and the double pass gain lowers the OPO oscillation threshold further.

Other choices of nonlinear crystal are possible in this range of operation one suitable material is orientation-patterned gallium arsenide (OP GaAs), others are silver gallium selenide ($AgGaSe_2$), gallium selenide (GaSe) and silver gallium sulphide ($AgGaS_2$). This embodiment is also arranged as a high repetition rate pulsed system by inclusion of Q-switch 203—as the person skilled in the art will appreciate, continuous wave or less rapidly pulsed systems can be provided using other component choices.

As is described above, an OPO produces a longer wavelength idler beam and a shorter wavelength signal beam. Either or both of the idler and the signal beam can be used for spectroscopic purposes. The advantage of using both beams is that this can extend the spectral range over which a single OPO can be used in the case of ZGP, this allows the use of the idler beam for essentially an LWIR region of operation (in the fingerprint region), with the signal beam providing coverage in the MWIR region. This is a significant advantage of this approach—using ZGP as the nonlinear crystal, radiation can be generated in both the 3-4 micron range and the 5-9 micron range with one system if both idler beam and signal beam are used. An alternative approach is to use multiple laser source sections with different nonlinear materials to cover different ranges—these could then be optimised to provide either the signal beam or the idler beam as output, if preferred. A suitable MWIR system would be that described in WO 2006/061567 A1, which uses periodically poled lithium niobate (PPLN) as a nonlinear medium.

A motion stage 207 is provided to move the nonlinear crystal 206 in order to tune the OPO to different output wavelengths. In the case of ZGP, the approach taken is to rotate the nonlinear crystal to tune it to a different wavelength. Phase matching is achieved in the nonlinear material, which is strongly birefringent, by using the different polarization states available—a tuning curve determining signal and idler wavelengths for given pump wavelengths is established for rotational angle of the nonlinear crystal. In the case of ZGP, 15 degrees of rotation of the crystal can tune the idler from 5 to 9 microns while tuning the signal between 2.7 and 3.8 microns. Motion stage 207 is in this case a rotation stage to which the nonlinear crystal 206 is bonded—conventional commercially available rotation stages provide sufficient accuracy for this purpose.

In the case of a periodically poled material (like PPLN), the motion stage 207 can be a translation stage, as the tuning is instead achieved by the poling separation, which is varied orthogonally to the direction of travel of light through the material, so translation of the nonlinear crystal 206 in this orthogonal direction can be used for tuning.

For effective detection of the presence or absence of an absorption in the target molecule, it is desirable for the linewidth of the output beam incident upon the target to be similar to or narrower than the linewidth of the spectral line resulting from that absorption. The system described provides generally suitable linewidths for the spectroscopy of hydrocarbons in the fingerprint region, but if narrower linewidths are required, the laser source section 200 may also be provided with an etalon.

Figure 3:
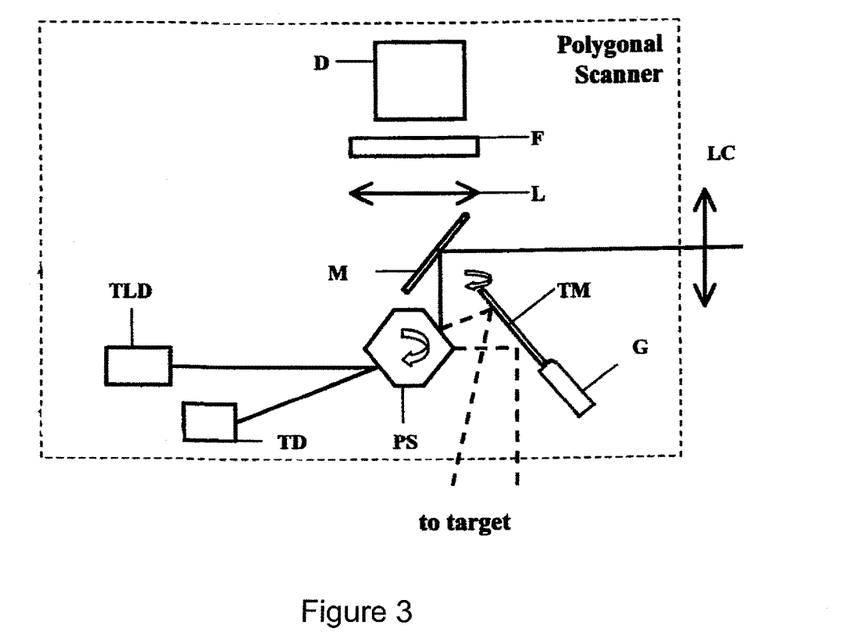
FIG. 3 shows a scanning system for use in embodiments of the invention.

An exemplary scanning system is shown in FIG. 3. The purpose of the scanning system is to scan the incident beam (whether signal, idler or both) across the target region in order to produce a rasterized scan, and so construct an image of the target region. The same optics are used to transmit the incident beam and to capture the backscattered beam for transmission to the detector system.

In the arrangement shown in FIG. 3, a collimating lens LC with high transmission in the relevant spectral region (e.g. calcium fluoride) collects the output beam from the OPO and this is directed by mirror m on to a first scanning mirror (in this case, polygonal scanner PS). Light from the first scanning mirror is reflected on to the second scanning mirror, tilting mirror TM. These two scanning mirrors provide two axes of the rasterised scan—polygonal scanner PS provides slower scanning along one (X) axis, whereas the tilting mirror TM driven by high speed galvanometer G provides the rapid scan along the Y axis for each X axis position.

Scanning is synchronised with the pulsed operation of the laser system. Use of Q-switching provides a rapidly pulsed pump laser, and so OPO output. Each pulse is sampled to provide a triggering signal, and the triggering signal is used to define a pixel. The scanning mirrors are synchronized with the pulsed operation of the laser so that the backscattered light received in the detection system can be interpreted as pixel data and hence as image data. The imaging system is also synchronized with translation of the translation stage 207 for the nonlinear medium, so individual image frames are associated with specified output beam wavelengths—in this way image frames may be assembled to form hyperspectral images.

Backscattered radiation from the target is incident on the second and first scanning mirrors, and is collected by collection lens L—optionally this may be followed by a filter F to exclude stray light. The backscattered light is then received by a detection system, as described in FIG. 4 below.

Figure 4:
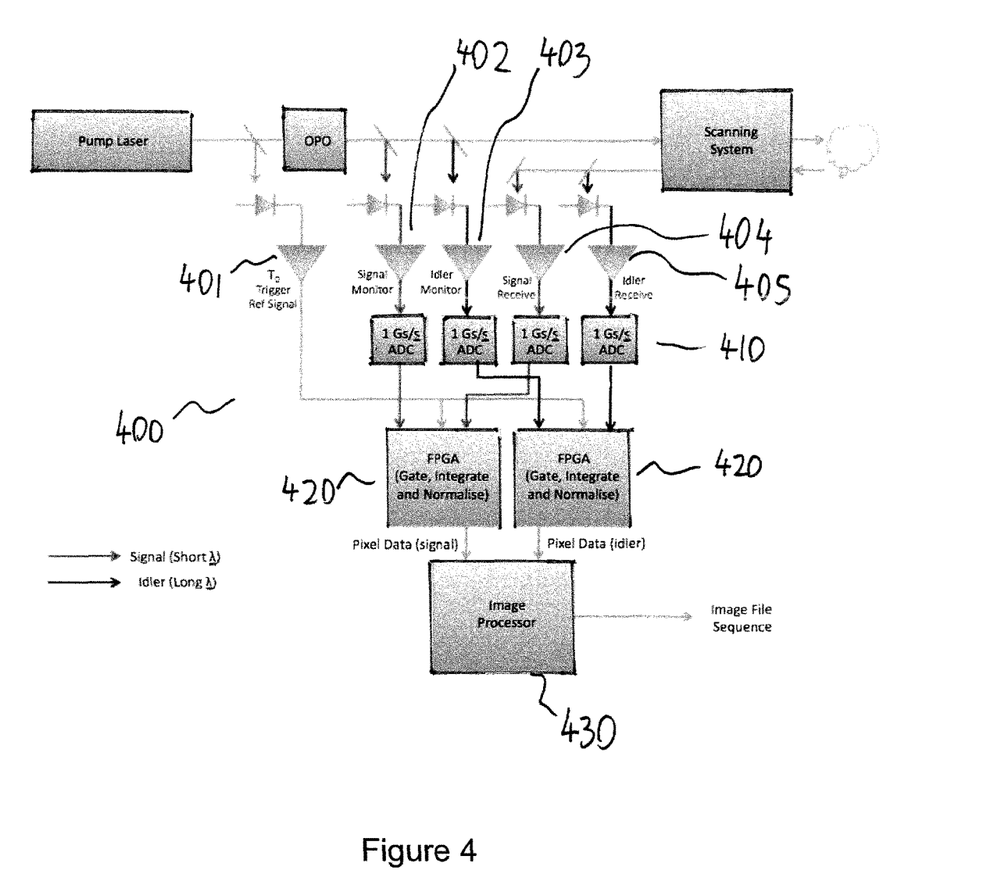
FIG. 4 shows schematically a detection system for use in embodiments of the invention.

FIG. 4 shows a detection system 400 adapted for using both the signal beam and the idler beam as the skilled person will appreciate, this approach can be used for signal beam—or idler beam only simply by removing the relevant components.

This system uses five detector elements. Pump monitor 401 is an ultrafast (20 ps) detector for generating a timing trigger reference signal for the system. Signal monitor 402 and idler monitor 403 are fast (2 ns) detectors sampling the energy of the signal beam and pump beam respectively. Signal receive 404 and idler receive 405 are fast (2 ns) low noise detectors that measure the received signal and idler wavelength energies as reflected from the target. These detectors may require thermoelectric cooling, particularly for longer wavelength use.

The detectors should be chosen appropriately for performance at the required wavelength. While suitable mirror materials (eg gold) and lens materials (eg ZnSe) may be used across a wide IR range, detectors will typically have a narrower range. However, HgCdTe (also known as MCT) is an effective solution over the 2-15 micron range. InAs is a possible solution up to approximately 8 microns. It may also be possible to use multiple detector ranges in the instrument, for example using InGaAs for MWIR use and HgCdTe for longer wavelengths.

The output pulses from the detectors pass to a circuit board containing for each detector a controllable gain pre-amplifier and a Gigasample per second (Gs/s) analogue to digital converter (ADC) 410. The outputs of each ADC goes to one of two field programmable gate arrays 420 (one for signal, one for idler) that, on receiving the pump monitor trigger pulse, sequentially writes the digital values into memory.

The FPGAs are configured for time of flight according to the round trip distance determined from the laser to the target and back. Between laser pulses the FPGA integrates the data values in memory, allowing for time of flight. All other signals are gated out and ignored. Four values for outgoing pulse energies and received pulse energies at signal and idler wavelengths result. Pulse-to-pulse energy variations are cancelled out by dividing the received pulse energy by the outgoing pulse energy to provide two pixel values, wavelength by wavelength. Each pixel, for an imaging system, is associated with a position in the target region determined by the scanning system, and can then be assembled into an image for that wavelength or pair of wavelengths. Different image frames may be provided at different wavelengths by translation of the nonlinear medium between frames. In this way a plurality of images are built up at a plurality of predetermined wavelengths. The image processing system 430 constructs these images and applies any desired image processing algorithms. The resulting image files may then be sent out through a suitable network connection for any further processing, viewing and storage.

Figure 5:
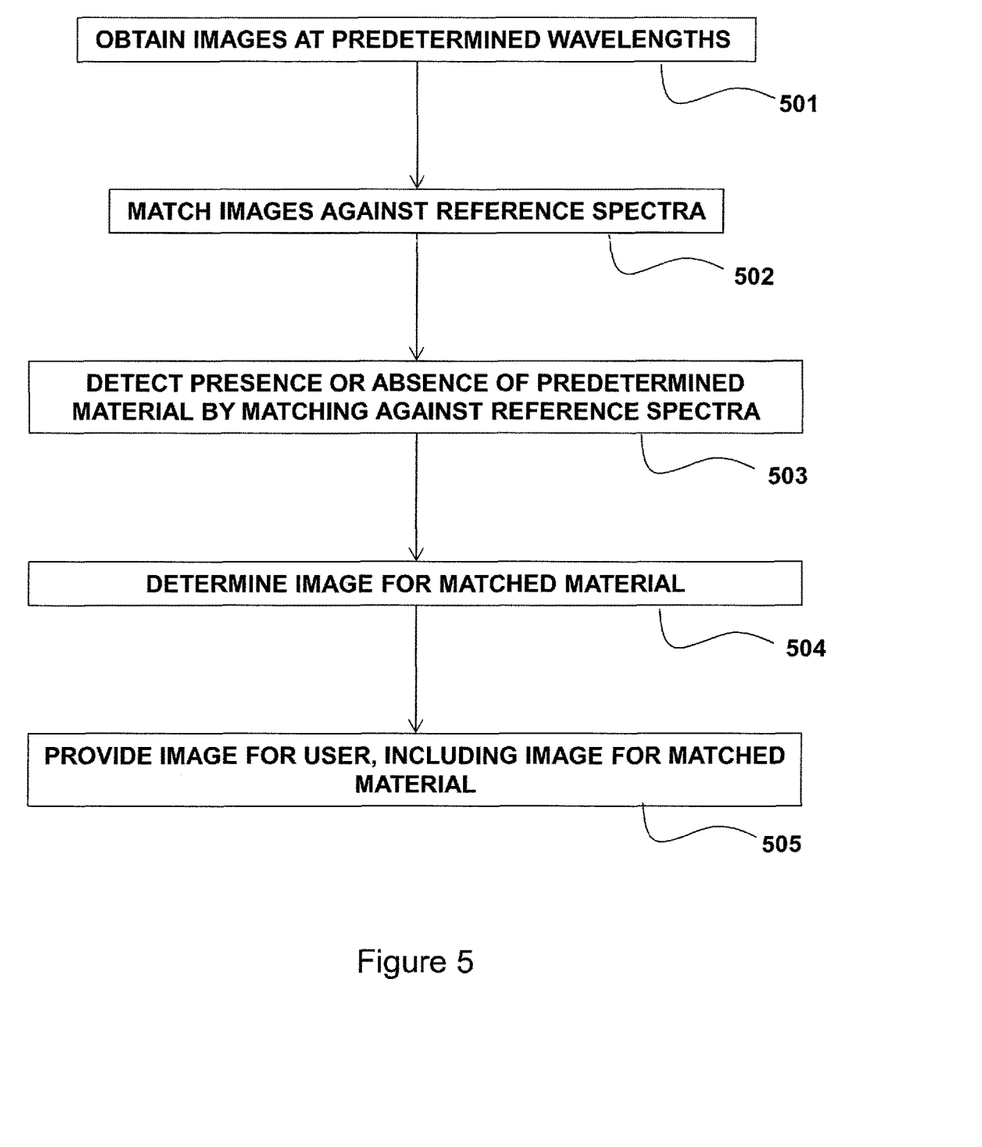
FIG. 5 illustrates schematically a process for recognising presence or absence of a predetermined volatile compound.

A process for detection of a predetermined material and preparation of a suitable image is described below with reference to FIG. 5.

Figure 6:
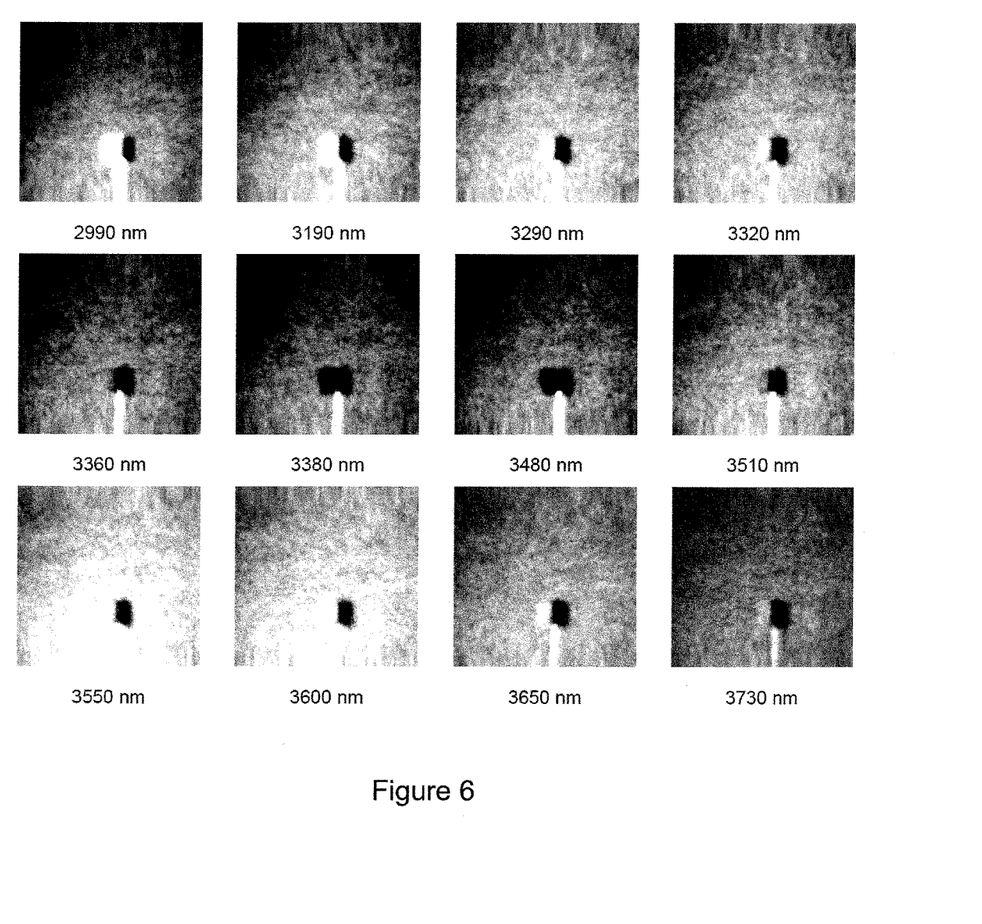
FIG. 6 illustrates imaging of a predetermined material using processes described in this specification to illustrate the results of using hyperspectral imaging for detection.

The initial output 501 of the hyperspectral imaging system described above is a series of images of a scene at different wavelengths—FIG. 6 provides an example of this (in this case, from the imaging of a solid sample of hexamine). These predetermined wavelengths will have been chosen to correspond to spectral features useful for determining the presence or absence of one or more predetermined materials. These features may be the presence or absence of a particular spectral feature—such as a specific band in the fingerprint region—or the relative intensity of at a series of particular wavelengths (for example, the relative intensity at a series of closely related wavelengths could allow the determination of the slope of a particularly broad spectral band). The detected imaging results can then be matched 502 against reference spectra. This may not be across the whole image—a particular region (for example, a region providing a signal in a particular fingerprint region band) may be used to identify an area of interest within the image, and only the pixels of the image in this area of interest may be considered in the matching and subsequent detection process.

The presence or absence of a predetermined material may thus be detected 503 by the result of the matching process. This process may be in multiple stages for example, MWIR bands may be used to identify a class of material, with specific lines within the LWIR fingerprint region used to identify specific molecules. As indicated previously, the linewidth of the laser source needs to be sufficiently narrow for effective detection of narrow spectral lines of interest. A practical threshold, dependent in practice on the sensitivity required, the tolerance of false results allowed, and the proximity of confusingly similar materials, needs to be established for each material to establish satisfactory detection.

For an imaging system, the image region over which the predetermined material has been detected needs to be determined 504. This may be determined on the basis of the region of the target image used in the determining step 503, but may also be reassessed and regions of the target image characterised as containing or not containing the predetermined material on the basis of a positive identification of presence of that material for a part of the image at least. The intensity of signal in all or part of the spectrum of the predetermined material may be used to assign a concentration to the material, or an intensity in the image representative of concentration.

The presence of the predetermined material needs to be shown 505 to the user. As recognition has taken place using a number of spectral bands, it may not be appropriate to do this by using a specific spectral image, but rather by using a false colour image with a specific false colour assigned to the predetermined material. This may be superposed on an image representative of the features of the scene (such as an image in the visible or the near infrared). The use of different false colours can then allow a number of different predetermined materials to be imaged in the same user image—in particular contexts (such as the remote detection of explosive materials), this may be particularly desirable.

The invention claimed is:

1. An infrared detection system, comprising:
a laser source comprising an optical parametric oscillator having a pump laser and a nonlinear medium, the laser source providing output radiation for illuminating a target, wherein the output radiation excludes a broadband output and is tuned to at least one wavelength in the fingerprint region of the infrared spectrum, and both an idler beam and a signal beam of the optical parametric laser are provided by the laser source,
wherein the idler beam is tuned to provide output radiation at least partly within the fingerprint region and the signal beam is tuned to provide output radiation at least partly at shorter wavelengths than in the fingerprint region;
wherein the idler beam, the signal beam, or both the idler beam and the signal beam of the optical parametric laser are provided as output radiation;
a detector configured to detect radiation backscattered from the target, wherein the detector comprises an imaging system;
an analyser adapted to match detected radiation signals against predetermined spectra to determine from at least the presence or absence of detected signal in said at least one wavelength whether a predetermined volatile compound is present; and
an imager adapted to provide an image of the target including an indication of whether the predetermined volatile compound is present.

2. The infrared detection system as claimed in claim 1, wherein the nonlinear medium comprises a $ZnGeP_2$ crystal.

3. The infrared detection system as claimed in claim 1, wherein the nonlinear crystal is disposed inside a cavity of the pump laser.

4. The infrared detection system as claimed in claim 1, further comprising a tuning mechanism to tune the output of the laser source between a plurality of wavelengths, wherein the infrared detection system is a hyperspectral detection system.

5. The infrared detection system as claimed in claim 4, wherein the analyser is adapted to determine from the presence or absence of detected signal in more than one wavelength of the plurality of wavelengths whether a predetermined volatile compound is present.

6. The infrared detection system as claimed in claim 1, wherein the one or more laser sources provide pulsed output radiation.

7. The infrared detection system as claimed in claim 6, wherein the infrared detection system provides an image in real time.

8. The infrared detection system as claimed in claim 6, wherein the infrared detection system comprises a scanning system for scanning a target region and the scanning system is synchronised with the pulsed output radiation.

9. The infrared detection system as claimed in claim 6, wherein the analyser determines a portion of an image where a predetermined material is present or absent.

10. The infrared detection system as claimed in claim 1, wherein the analyser matches detected radiation signals against predetermined spectra at a plurality of wavelengths determined for that predetermined material.

11. The infrared detection system as claimed in claim 10, wherein at least some of the plurality of wavelengths lie in the fingerprint region.

12. A method of determining the presence or absence of a predetermined volatile compound comprising:

illuminating a target with radiation from a laser source, the laser source comprising an optical parametric oscillator having a pump laser and a nonlinear medium, wherein the output radiation excludes a broadband output and is tuned to at least one wavelength in the fingerprint region of the infrared spectrum, and both an idler beam and a signal beam of the optical parametric laser are provided by the laser source, wherein the idler beam is tuned to provide output radiation at least partly within the fingerprint region and the signal beam is tuned to provide output radiation at least partly at shorter wavelengths than in the fingerprint region;

wherein the idler beam, the signal beam, or both the idler beam and the signal beam of the optical parametric laser are provided as output radiation;

detecting radiation backscattered from the target, wherein the detecting step comprises an imaging step;

determining by matching detected radiation signals against predetermined spectra from at least the presence or absence of detected signal in said at least one wavelength whether a predetermined volatile compound is present; and providing an image of the target including an indication of whether the predetermined volatile compound is present.

* * * * *